United States Patent [19]

Palepu et al.

[11] Patent Number: 5,690,959
[45] Date of Patent: Nov. 25, 1997

[54] PHARMACEUTICAL THERMAL INFUSION PROCESS

[75] Inventors: Nageswara R. Palepu, Lansdale; Gopadi M. Venkatesh, King of Prussia, both of Pa.

[73] Assignee: SmithKline Beecham Corporation, Philadelphia, Pa.

[21] Appl. No.: 433,368
[22] PCT Filed: May 26, 1994
[86] PCT No.: PCT/US94/05930
§ 371 Date: May 4, 1995
§ 102(e) Date: May 4, 1995
[87] PCT Pub. No.: WO94/27557
PCT Pub. Date: Dec. 8, 1994

[30] Foreign Application Priority Data

| May 29, 1993 | [GB] | United Kingdom | 9311188 |
| Aug. 5, 1993 | [GB] | United Kingdom | 9316252 |
| Sep. 11, 1993 | [GB] | United Kingdom | 9318920 |

[51] Int. Cl.⁶ .................................................. A61K 9/24
[52] U.S. Cl. .......................... 424/472; 424/461; 424/470; 424/489
[58] Field of Search ........................ 424/489, 490, 424/499, 472

[56] References Cited

U.S. PATENT DOCUMENTS

| 2,793,979 | 5/1957 | Svedres | 167/82 |
| 2,887,438 | 5/1959 | Summit et al. | 167/82 |
| 2,951,792 | 9/1960 | Swintosky | 167/82 |
| 3,279,998 | 10/1966 | Raff et al. | 167/82 |
| 3,487,138 | 12/1969 | Hess et al. | 264/112 |
| 4,132,753 | 1/1979 | Blichare et al. | 264/25 |
| 4,380,534 | 4/1983 | Fukui et al. | 424/38 |
| 4,935,246 | 6/1990 | Ahrens | 424/490 |
| 5,023,089 | 6/1991 | Sakamoto et al. | 424/489 |
| 5,169,645 | 12/1992 | Shukla et al. | 424/499 |

FOREIGN PATENT DOCUMENTS

WO 93/18753  9/1993  WIPO.

OTHER PUBLICATIONS

J. Pharmacobio–Dyn, 9 pp. 631–637 (1986).
Chem. Pharm. Bull, vol. 37 No. 12 pp. 3416–3419 (1989).
J. Pharmacobio–Dyn, 9 13 (1986).
Drug Development and Industrial Pharmacy, 16(13), pp. 1963–1969 (1990).
Proceed. Intern. Symp. Control. Rel. Bioact. Mater. 14 pp. 192–193 (1987).
J. Microencapsulation, vol. 1, No. 2, pp. 137–155 (1984).
Drug Development and Industrial Pharmacy, 16(8), pp. 1375–1389 (1990).
Pharmaceutical Research, vol. 7, No. 11 (1990).
Int'l. J. of Pharmaceutics, 78 pp. 35–41 (1992).

*Primary Examiner*—Thurman K. Page
*Assistant Examiner*—William E. Benston, Jr.
*Attorney, Agent, or Firm*—Wayne J. Dustman; Charles M. Kinzig; Edward T. Lentz

[57] ABSTRACT

A chewable tablet comprises a medicament dispersed in a chewable base, such as mannitol, together with an effervescent couple, such as citric acid—sodium bicarbonate. The combination of effervescence and chewability with optional flavorings improves the taste characteristics of the medicament in oral administration. A disintegrant such as microcrystalline cellulose may be added to give the patient the option of dispersing the tablet in water.

34 Claims, 1 Drawing Sheet

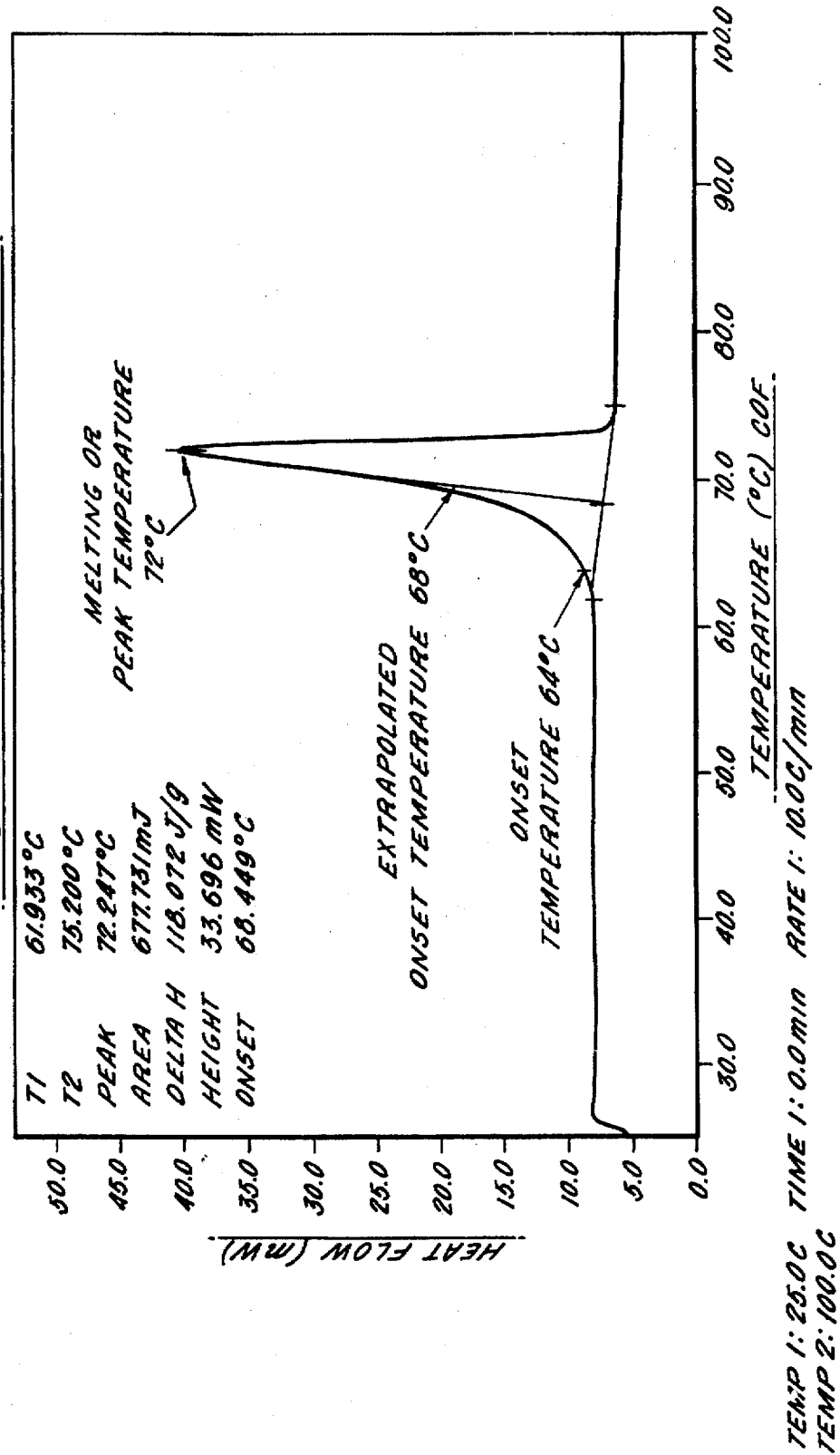

PHARMACEUTICAL THERMAL INFUSION PROCESS

FIELD OF THE INVENTION

This invention relates to a thermal infusion process for preparing controlled release solid dosage forms of medicaments for oral administration and controlled release solid dosage forms of medicaments prepared thereby. More specifically, controlled release solid dosage forms of amoxicillin, clavulanate and mixtures thereof are prepared according to this invention.

BACKGROUND OF THE INVENTION

It is desirable to provide pharmaceutical formulations for oral administration in a form in which a delayed or controlled release of the active materials within the formulation is achieved, so that complete release of the active materials into solution in the body of the patient from the formulation occurs over a prolonged period after oral administration, so that for example the formulation need only be taken twice or even only once a day.

Various methods of formulating pharmaceutically active compounds for oral administration so that the release of the active compound(s) in the formulation takes place over a prolonged period after ingestion are known. For example, tablets maybe made which are coated with a controlled release material, such as a polymer or a wax. Encasing tablets is useful in delaying the initial release of the active compound but generally contributes little toward controlling the release of the medicament subsequent to in vivo removal of the coating.

Pharmaceutically active compounds may be incorporated into a matrix with a relatively impermeable polymer. Compounds which are moisture sensitive, however, are considered inappropriate candidates for matrixed polymeric controlled release formulations because of the degradation which occurs in the time taken to diffuse out of the matrix after dissolution. Additionally, the dissolution profile of matrixed polymeric controlled release formulations generally relies on dissolution followed by diffusion to liberate the medicament from the matrix thereby subjecting moisture sensitive compounds to aqueous degradation prior to in vivo release.

Solvent based mediums used in the preparation of matrixed polymeric formulations and other controlled release formulations are either environmentally unsound due to the release of solvent into the atmosphere or expensive due to the cost of maintaining solvent recovery systems for such process. Further, solvent based mediums of hydrophobic waxy material used in the preparation of controlled release formulations generally require a large surface area and significant time (often a week or more) to provide for proper annealing of the coating material in order to achieve proper control of the release of medicament from the solid dosage form.

Additionally, melt granulation methods have been employed in formulating controlled release dosage forms of pharmaceutically active compounds. Conventional melt granulation processes are characterized by the melting of a controlled release wax and then dispersing the medicament throughout the melt. The melted material is allowed to congeal and the solidified mass is sized and compressed into tablets. It is apparent that there are disadvantages associated with this method of preparing a sustained release tablet. First, heat labile compounds will decompose in the molten wax. Further, it is expensive and hazardous to adopt this molten wax technique to mass production. Aside from the hazard of working with large quantities of molten wax, there is the difficulty of working with the hard congealed-medicament mixture which must be removed from the mixing vessel and sized. Additionally, the sizing of the hard congealed-medicament mixture exposes the previously encased medicament thereby detracting from its controlled release profile in subsequent dosage forms. A further outstanding disadvantage of the known art method of preparing sustained release tablets, in particular by the molten wax process, is that a high dosage drug cannot be easily prepared with satisfactory release characteristics.

Some of the above described disadvantages are overcome by spraying the molten wax into a fluid bed of medicament particles to form coated granules. Spraying molten wax, however, requires that the control release wax be sprayed at a temperature of about 60°–80° C. above the melting point of the wax, thereby rendering such a process unusable for heat labile compounds.

Granulating the controlled release wax and pharmaceutically active material at ambient temperature is also known to prolong the release of medicaments. This method of granulation, however, fails to suitably envelop the medicament with control release material, thus allowing fluids to permeate the granulate and contact the medicament thereby degrading moisture sensitive medicament prior to in vivo release and allowing highly water soluble medicaments to quickly leach out of the granulate. As such, the effectiveness of ambient granulation of pharmaceutically active materials and control release wax in preparing prolonged release compositions of medicaments is limited to water stable medicaments which are minimally soluble.

Thus, there is a need in the art for a safe, economical, reliable and environmentally friendly method to formulate pharmaceutically active materials in controlled release formulations.

Particular problems occur in the co-formulation of amoxicillin trihydrate and clavulanate for delayed or controlled release applications. Amoxicillin trihydrate is only slightly soluble in water whereas salts of clavulanic acid are, in general, freely water soluble, heat labile and highly moisture sensitive and undergo spontaneous hydrolytic degradation when contacted by water. As such, the more soluble clavulanate will be released from a coated or matrix tablet of the co-formulated product at a significantly faster rate than the less soluble amoxicillin. It is therefore difficult to prepare such co-formulations from which amoxicillin and clavulanate are released by controlled dissolution at compatible rates.

Presently, co-formulations of amoxicillin and clavulanate are commercially available (under the tradename Augmentin®) only in immediate release dosage forms. Typically the commercially available formulation of Augmentin® comprises dry granulated film-coated tablets containing various amounts of: amoxicillin trihydrate; potassium clavulanate; colloidal silica (Cab-O-Sil or Aerosil 200); sodium starch glycolate (Explotab); magnesium stearate; and microcrystalline cellulose (Avicel).

In addition to the administrative advantages associated with a twice a day or a once a day dose regimen, a controlled release dosage formulation of Augmentin® would alleviate the undesirable side effects and gastric intolerance associated with the immediate release of a therapeutic dose of clavulanate.

We have now discovered a suitable controlled release oral formulation for use with co-formulations of amoxicillin and salts of clavulanic acid when prepared by the process of this invention. Said controlled release oral formulation providing significant protection against moisture (i.e. hydrolytic degradation) to clavulanic acid. Other objects of this invention will be apparent from the following description.

SUMMARY OF THE INVENTION

This invention relates to a thermal infusion process for preparing controlled release solid dosage forms of medicaments for oral administration and to the controlled release solid dosage forms of medicaments prepared by said process.

Preferably, this invention relates to a thermal infusion process for preparing controlled release solid dosage forms of heat labile, moisture sensitive or heat labile and moisture sensitive pharmaceutically active materials.

This invention also relates to controlled release solid dosage forms of amoxicillin, clavulanic acid and mixtures of amoxicillin and clavulanic acid prepared using the presently invented thermal infusion process.

Additionally, this invention relates to a method of transporting clavulanate and compositions containing clavulanate.

BRIEF DESCRIPTION OF THE DRAWINGS

FIG. 1 is a thermal analysis of glyceryl behenate used to demonstrate terms describing temperature as used herein.

"Onset temperature" is that temperature when the thermal transition signal in the DSC (differential scanning calorimetry) or DTA (differential thermal analysis) just leaves the baseline. For glyceryl behenate the onset temperature is at about 64° C.

The "melting or peak temperature" is the temperature represented by the apex of the peak. Glyceryl behenate melts at about 72° C.

The "extrapolated onset temperature" represents that temperature corresponding to the intersection of the pre-transition baseline with the extrapolated leading edge of the endotherm (melting curve). For glyceryl behenate the extrapolated onset temperature is at about 68° C.

DETAILED DESCRIPTION OF THE INVENTION

The present invention relates to a process for preparing controlled release solid dosage forms of pharmaceutically active materials which comprises the thermal infusion of a pharmaceutically active material and a hydrophobic waxy material into thermal infusion granules.

In utilizing the presently invented process a pharmaceutically active material and a hydrophobic waxy material are blended in a suitable mixer. The blend is optionally compacted, then subjected to thermal infusion by granulating in a granulator at a suitable thermal infusion temperature, preferably using a fluid bed granulator. A kettle granulator equipped with a temperature controller, a heat source, preferably a hot air supply or heating jacket and mixing blades or a rotating drum coating pan equipped with a heat source, preferably a heating jacket or hot air supply may also be employed. The granulation is cooled preferably at a controlled rate and optionally milled and screened in order to obtain granules with a desired particle size distribution. Advantageously, if the hydrophobic waxy material and/or pharmaceutically active material are not compacted prior to thermal infusion the post thermal infusion mixture is milled and screened into granules of desired particle size distribution. The granules thus obtained (hereinafter "thermal infusion granules") are formulated into solid dosage forms of desired strength. In the presently invented process, and in all modifications thereof, optional pharmaceutically acceptable excipients, optional medicaments or additional hydrophobic waxy materials or a combination thereof may be blended with the pharmaceutically active material prior to, post or prior to and post thermal infusion. Further, the pharmaceutically active material may be compacted prior to blending with a hydrophobic waxy material.

Advantageously the pharmaceutically active material and hydrophobic waxy material and optional additives are compacted prior to being thermally infused. Exemplary of the modifications within the scope of the above processes which are included in the invention include the preferred process wherein dry blends of the medicament(s) and hydrophobic waxy material are compacted and milled into granules of suitable size distributions. Said granules are subjected to thermal infusion and pressed into tablets. The tablets thus obtained may contain only one medicament or may contain multiple medicaments. Additionally, the medicaments may be contained in the same or separate layers of a compressed tablet.

By the term "thermal infusion" and derivatives thereof, as used herein is meant that the subject pharmaceutically active material is blended with a hydrophobic waxy material and optional additives and then optionally compacted, followed by granulation in a granulator at a suitable thermal infusion temperature and then optionally milled and screened to form thermal infusion granules.

By the term "thermal infusion process" and derivatives thereof, as used herein is meant the thermal infusion of a pharmaceutically active material, a hydrophobic waxy material and optional additives to form thermal infusion granules, as described above, and then optionally preparing solid dosage forms of said granules.

When referring to thermally infusing blends in which the percentage of hydrophobic waxy material is 20% by weight or greater, preferably 30% or greater, in relation to the subject pharmaceutically active material, the term "suitable thermal infusion temperature" or "thermal infusion temperature" and derivatives thereof, as used herein is meant a temperature above ambient temperature and below the melting point of the subject hydrophobic waxy material, preferably below the extrapolated onset temperature of the subject hydrophobic waxy material, preferably at a temperature of from about 5° to about 25° C. below the extrapolated onset temperature of the subject hydrophobic waxy material, most preferably at a temperature of from about 5° to about 15° C. below the extrapolated onset temperature of the subject hydrophobic waxy material.

When referring to thermally infusing blends in which the percentage of hydrophobic waxy material is less than 20% by weight, preferably less than 15%, in relation to the subject pharmaceutically active material, the term "suitable thermal infusion temperature" or "thermal infusion temperature" and derivatives thereof, as used herein includes temperatures above the extrapolated onset temperature, preferably less than 15° C. above the melting temperature, of the hydrophobic waxy material.

The desired percentage of particular hydrophobic waxy material for use with a particular pharmaceutically active material in the presently invented process will depend to a great extent on the solubility of pharmaceutically active material. The more soluble the pharmaceutically active material is, the higher the percentage of hydrophobic waxy material needed to provide acceptable controlled release. As such, the appropriate ratio of a particular hydrophobic waxy material to a particular pharmaceutically active material is readily ascertainable by one of skill in the art as indicated herein.

When the percentage of hydrophobic waxy material is 20% by weight or greater, and particularly when it exceeds 30%, in relation to the pharmaceutically active material, conducting the presently invented thermal infusion process at a temperature above the extrapolated onset temperature begins to result in the formation of agglomerates which must be sized before being formulated into solid dosage forms. Since the sizing of the formed agglomerates breaks the continuous barrier around the medicament, the release from granules prepared thereby is not sufficiently controlled.

In utilizing the presently invented process when the percentage of hydrophobic waxy material is less than 20% by weight, particularly when it is less than 15%, in relation to the pharmaceutically active material the granules fail to form agglomerates even when granulated at temperatures above the melting point of the wax. As such, conducting a thermal infusion process at temperatures above the melting point of the waxy material when the wax content of the wax pharmaceutically active compound blend is less than 20% provides for quicker formation of a continuous waxy barrier around the medicament.

The term describing temperature as used herein, are defined below.

"Onset temperature" is that temperature when the thermal transition signal in the DSC (differential scanning calorimetry) or DTA (differential thermal analysis) just leaves the baseline. For glyceryl behenate the onset temperature is at about 64° C.

The "melting or peak temperature" is the temperature represented by the apex of the peak. Glyceryl behenate melts at about 72° C.

The "extrapolated onset temperature" represents that temperature corresponding to the intersection of the pre-transition baseline with the extrapolated leading edge of the endotherm (melting curve). For glyceryl behenate the extrapolated onset temperature is at about 68° C.

The presently invented thermal infusion process is particularly advantageous in that it provides for the diffusion (migration) of the wax molecules in the thermal infusion granules to the surface, which coalesces and forms a continuous, uniform barrier around the medicament. The uniform coating is achieved regardless of the original particle shape and size distribution. This barrier controls the release of the medicament from subsequently formulated solid dosage forms. The thickness of the barrier, and thus the extent of the delay of the release of the subject medicament, can be varied by adjusting the ratio of hydrophobic waxy material to medicament introduced into the subject thermal infusion process. Further, since the presently invented thermal infusion process can be consistently utilized in large scale granulators, it provides for an economical and environmentally friendly method to prepare controlled release formulations of pharmaceutically active materials on an industrial scale. Advantageously, large scale granulations are performed in a fluid bed granulator. This invention represents the first demonstration of a fluid bed granulator utilized to provide for the diffusion of wax molecules from a compacted blend, to form a uniform barrier around medicament particles of non uniform size and shape distributions to form controlled release granules. As such, the presently invented process i) avoids degradation of heat sensitive medicaments (such as clavulanate)

ii) avoids formation of agglomerates which would otherwise need to be broken down (sized) prior to further processing (capsule filling or tableting)

iii) is cost effective in that it utilizes less hydrophobic waxy material and iv) can be readily utilized in large scale operations.

By the term "compacted" and derivatives thereof, as used herein, unless otherwise defined, is meant that the subject material, preferably a hydrophobic waxy material and additives are compressed, preferably slugged using a suitable tablet press or roller compacted and then milled and screened to obtain a suitable particle size distribution.

By the term "solid dosage form" and derivatives thereof, as used herein is meant thermal infusion granules or that the prepared thermal infusion granules and optional additives, including optional medicaments, are formulated into orally administerable forms, preferably filled gelatin capsules or compressed into tablets.

By the term "pharmaceutically active material" and derivatives thereof, as used herein is meant a solid material which exhibits therapeutic activity when administered internally to an animal, preferably a mammal, including a human, and controlled release formulations thereof. Examples of a pharmaceutically active material, as described above, includes; cimetidine and lithium carbonate.

By the term "cimetidine" as used herein is meant a compound of the formula

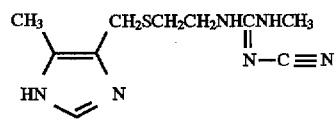

and pharmaceutically acceptable salts thereof. Chemically, cimetidine is designated as N"-cyano-N-methyl-N'-[2-[[(5-methyl-1-H-imidazol-4-yl)methyl]thio]-ethyl]-guanidine. Cimetidine is a histamine $H_2$-receptor antagonist and is commercially available under the trade name Tagamet®.

Lithium carbonate is indicated in the treatment of manic episodes of manic-depressive illness and is commercially available under the tradename Eskalith®.

The process of the present invention is particularly advantageous in preparing controlled release solid dosage forms of pharmaceutically active materials which are heat labile and/or moisture sensitive.

By the term "moisture sensitive" as used herein is meant pharmaceutically active materials which undergo spontaneous hydrolytic degradation of at least 1% when contacted by water.

By the term "heat labile" as used herein is meant a pharmaceutically active compound which undergoes a minimum of 1% degradation at about 90° C.

Preferred heat labile and/or moisture sensitive pharmaceutically active materials which can benefit from the presently invented process are antibacterial agents and beta-lactamase inhibitors.

Preferred antibacterial agents for use in the presently invented process and formulations prepared thereby are beta-lactam antibiotics, such as penicillins and cephalosporins, a particularly preferred penicillin being amoxicillin, typically as its trihydrate. The antibacterial agent may be co-formulated with a beta-lactamase inhibitor, preferably clavulanate, particularly potassium clavulanate.

When utilizing a particular heat labile medicament according to the present invention one skilled in the art can readily determine the appropriate control release wax by selecting a hydrophobic waxy material which displays a thermal infusion temperature below the temperature at which the subject pharmaceutically active material experiences a 1% degradation.

When utilizing a moisture sensitive medicament according to the present invention the selected hydrophobic waxy material is preferably used in an anhydrous form.

By the term, "amoxicillin" as used herein is meant a compound of the formula

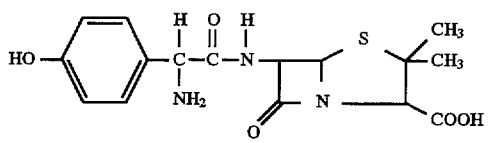

and pharmaceutically acceptable salts, hydrates, solvates, and esters thereof. Chemically, amoxicillin is designated as D-(-)α-amino-p-hydroxybenzyl-penicillin.

Amoxicillin is a known β-lactam antibiotic compound and is commercially available and generally used in the form of a trihydrate under the trade name Amoxil®.

By the term "clavulanic acid" as used herein is meant a compound of the formula

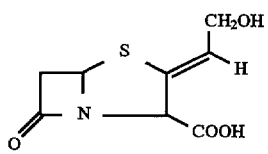

and pharmaceutically acceptable salts, hydrates, solvates and esters thereof.

Chemically, clavulanic acid is designated as Z-(3R,5R)-2-(β-hydroxyethyldiene) clavam-3-carboxylate. Clavulanic acid is a known β-lactamase inhibiting compound and is commercially available in the form of a potassium salt (clavulanate potassium).

By the term "clavulanate" as used herein is meant the potassium salt of clavulanic acid or potassium clavulanate.

Clavulanate is a heat labile-moisture sensitive compound.

By the term "immediate release or (IR)" as used herein is meant that the subject medicament is added, to post thermal infusion granules, in a form, including granules of the medicament itself or its (IR) granules, suitable to provide a rapid release portion of the subject medicament in subsequently formulated solid dosage forms.

By the term "immediate release (IR) granules" as used herein is meant non thermally infused granules of a medicament and a hydrophobic waxy material in a ratio which when formulated in solid dosage forms provides for rapid release of the medicament.

Preferably IR granules of clavulanate and glyceryl behenate when utilized according to the present invention will be in the range of from about 20% to 80% by weight of clavulanate, most preferably about 70%.

Preferably IR granules of amoxicillin trihydrate and glyceryl behenate when utilized according to the present invention will be in the range of from about 75% to 98% by weight of amoxicillin trihydrate most preferably about 90%.

By the term "controlled release or (CR)" and derivatives thereof, as used herein is meant that the subject medicament is added, to pre or post thermal infusion granules in a form, including thermal infusion granules, suitable to provide a hydrocontrolled release portion of the subject medicament in subsequently formulated solid dosage forms.

By the term "medicament" as used herein is meant a pharmaceutically active material or a bioactive material as defined herein either in immediate release or controlled release form.

By the term "bioactive material" and derivatives thereof, as used herein is meant a solid material which exhibits therapeutic activity when administered internally to an animal, preferably a mammal, including a human, either in immediate release or controlled release form and which is suitable for co-administration with a pharmaceutically active material, as defined herein.

By the term "compressed into tablet" and derivatives thereof as used herein, unless otherwise defined, is meant that presently prepared thermal infusion granules, optional additional medicaments, optional additional hydrophobic waxy materials or optional pharmaceutically acceptable excipients or a combination hereof utilized in the presently invented process are blended and compressed into a single tablet or separately formulated and compressed into bi or tri layer tablets.

By the term "hydrophobic waxy material", "waxy material" or "wax" as used herein, is meant a fatty acid, alcohol or ester, alone or an admixture thereof. More specifically, the fatty acid may have from about 10 to about 22 carbon atoms and may be, for example, decanoic, stearic, palmitic, lauric or myristic acid.

The fatty alcohols may have from about 14 to about 31 carbon atoms and may be, for example, lauryl alcohol, cetyl, stearyl, myristyl, carbucyl or ceryl alcohol.

The esters may be mono-, di-, or triglyceryl esters. The hydrophobic waxy material may be modified by waxy materials of natural or synthetic sources. Exemplary of such waxes are beeswax, spermaceti wax or carnauba wax.

Preferred hydrophobic waxy materials for use herein include: cetyl alcohol, carnauba wax, glyceryl behenate (Compritol® from Gattefosse Corp.) glyceryl palmitostearate (Precirol® from Gattefosse Corp.) glyceryl monostearate and glyceryl distearate.

Pharmaceutically acceptable excipients are optionally utilized in the presently invented process in order to further modify the release characteristics of the controlled release tablets.

Preferred pharmaceutically acceptable excipients for use herein include: microcrystalline cellulose (e.g., Avicel®, a diluent from FMC Corp.), colloidal silicon dioxide (e.g., Cab-O-Sil, a glidant from Cabot Corp.), sodium starch glycolate (a tablet disintegrant), an enteric polymer (e.g., Eudragit L polymer from Rohm Pharma), a soluble filler (e.g., mannitol, sorbitol or lactose) and insoluble filler (e.g., dicalcium phosphate or its dihydrate).

Sodium starch glycolate is a tablet disintegrant which helps break up of the tablet into particles, colloidal silicon dioxide is a glidant which improves the flow of powdered material; Eudragit L polymer, an enteric polymer which may delay the release of the active from the tablet at lower pHs in the gastrointestinal tract; lactose, a soluble filler which help imbibe water into the tablet; dicalcium phosphate, an insoluble filler which may hinder water imbibition into the tablet while Avicel, microcrystalline cellulose, generally improves the compactability of formulations and modifies the release rate by its wicking action.

Particularly preferred among the above pharmaceutically acceptable excipients are: Microcrystalline cellulose, lactose and dicalcium phosphate dihydrate.

In utilizing the presently invented process, a pharmaceutically active material, preferably clavulanate, and a hydrophobic waxy material, preferably glyceryl behenate, are uniformly blended in a suitable mixer. This blend is compacted then subjected to thermal infusion, preferably at a temperature from about 5° to 25° C. below the extrapolated onset temperature of the hydrophobic waxy material, advantageously from 5° to 15° C. below the extrapolated onset temperature of the hydrophobic waxy material, preferably using a fluid bed granulator or a granulator equipped with a temperature controller, a heat source, preferably a hot air supply or heating jacket and mixing blades or a rotating drum coating pan equipped with a heat source, preferably a heating jacket or hot air supply. The heated thermally infused granules are preferably cooled to ambient temperature at a controlled rate in order to permit proper annealing of the outer wax barrier. The thermal infusion granules thus obtained and optional thermal infusion granules of amoxicillin, immediate release (IR) granules of clavulanate and immediate release (IR) granules of amoxicillin are formulated into solid dosage forms of desired strength.

When preparing a controlled release dosage form of amoxicillin according to the presently invented process thermally infused granules prepared from amoxicillin, hydrophobic waxy material, preferably glyceryl behenate, and optional pharmaceutically acceptable excipients may be blended with amoxicillin or its immediate release (IR) granules, thereby providing an immediate release portion of amoxicillin prior to formulation into solid dosage forms. Preferably the amoxicillin contained in a solid dosage form prepared according to the present invention will be in an amount suitable for co-administration with clavulanate. Particularly preferred are solid dosage forms containing from 200 mg to 1000 mg of amoxicillin.

When preparing a controlled release dosage form of clavulanate according to the presently invented process thermally infused granules of clavulanate prepared from clavulanate, hydrophobic waxy material, preferably glyceryl behenate, and optional pharmaceutically acceptable excipients may be blended with clavulanate, or its IR granules, thereby providing an immediate release portion of clavulanate, prior to formulation into solid dosage forms. Preferably the clavulanate contained in a solid dosage form prepared according to the present invention will be in an amount suitable for co-administration with amoxicillin. Particularly preferred are solid dosage forms tablets containing from 50 to 250 mg of clavulanate.

When utilizing amoxicillin and clavulanate together in the presently invented process, thermally infused granules of amoxicillin and thermally infused granules of clavulanate and optional pharmaceutically acceptable excipients are blended together, preferably in a ratio of from 12:1 to 1:1, by weight of amoxicillin/clavulanate respectively, most preferably from 10:1 to 3:1, in order to produce controlled release solid dosage forms. The thermally infused granules of amoxicillin and thermally infused granules of clavulanate and optional pharmaceutically acceptable excipients, in a ratio of from 12:1 to 1:1, by weight of amoxicillin/clavulanate respectively, most preferably from 10:1 to 3:1, may be separately compressed into bi or tri-layer tablets. Optionally, the thermally infused granules of amoxicillin and/or thermally infused granules of clavulanate are blended with amoxicillin or its IR granules and/or clavulanate or its IR granules prior to formulation into controlled release solid dosage forms, thereby providing an immediate release portion of these medicaments.

In a preferred embodiment of the presently invented process, thermally infused granules of amoxicillin and glyceryl behenate containing from about 50% to 98% by weight of the active material preferably about 90% of the active material are blended with microcrystalline cellulose in a range of from about 5% to 50% by weight of microcrystalline cellulose preferably about 15% by weight of microcrystalline cellulose and compressed into tablets using a suitable press. Said granules are preferably obtained by compacting uniform blends of amoxicillin, hydrophobic waxy material, preferably glyceryl behenate, and optional pharmaceutically acceptable excipients, milling and screening these compacts in order to obtain granules of a suitable particle size distribution, preferably from about 50 µm to 1000 µm and subsequently subjecting the same to thermal infusion. Preferably said thermal infusion will take place in a fluid bed granulator by raising the temperature of the fluidized blend from ambient (about 18° C.) to about 50° C. over a period of about 10 minutes, maintaining the temperature for about 25 minutes and cooling to ambient temperature over a period of about 15 minutes to prepare thermal infusion granules. Optionally, the thermally infused granules of amoxicillin blended with microcrystalline cellulose may be blended with thermally infused granules of clavulanate, preferably in a ratio of from 12:1 to 1:1 by weight of amoxicillin/clavulanate respectively, and compressed into tablets or the thermally infused granulations containing amoxicillin and thermally infused granulations containing clavulanate may be separately compressed into bi or tri-layer tablets. Optionally, the thermally infused granules of amoxicillin and thermally infused granules of clavulanate may be blended with amoxicillin or its IR granules and/or clavulanate or its IR granules prior to formulation into controlled release solid dosage forms, thereby providing an immediate release portion of these medicaments.

In a preferred embodiment of the presently invented process thermally infused granules of clavulanate and glyceryl behenate containing from 20% to 80% by weight of the active material preferably about 55% of the active material are compressed into tablets using a conventional tablet press. Said granules are preferably obtained by compacting uniform blends of clavulanate, hydrophobic waxy material, preferably glyceryl behenate, and optional pharmaceutically acceptable excipients, milling and screening these compacts in order to obtain granules of a suitable particle size distribution, preferably from about 50 µm to 1000 µm and subsequently subjecting the same to thermal infusion. Preferably said thermal infusion will take place in a fluid bed granulator by raising the temperature of the fluidized blend from ambient (about 18° C.) to about 50° C. over a period of about 10 minutes, maintaining the temperature for about 25 minutes and cooling to ambient temperature over a period of about 15 minutes to prepare thermal infusion granules. Optionally, the thermally infused granules of clavulanate may be blended with thermally infused granules of amoxicillin, preferably in a ratio of from 12:1 to 1:1 by weight of amoxicillin/clavulanate respectively, and compressed into tablets or the thermally infused granulations containing clavulanate and thermally infused granulations containing amoxicillin may be separately compressed into bi or tri-layer tablets. Optionally, the thermally infused granules of clavulanate and thermally infused granules of amoxicillin may be blended with clavulanate or its IR granules and/or amoxicillin or its IR granules prior to formulation into controlled release solid dosage forms thereby providing an immediate release portion of these medicaments.

In a particularly preferred embodiment of the presently invented process thermally infused granules of amoxicillin in an amount of from 50% to 98% by weight of the active material are blended with glyceryl behenate in an amount of from 40% to 2% by weight of glyceryl behenate, and colloidal silicon dioxide, in an amount of from 3% to 0.5% by weight of colloidal silicon dioxide, and compressed into tablets using a conventional tablet press. Optionally, said thermally infused granules of amoxicillin blended with glyceryl behenate and colloidal silicon dioxide may be blended with thermally infused granules of clavulanate, preferably in a ratio of from 12:1 to 1:1, of amoxicillin/clavulanate, respectively and compressed into tablets or the thermally infused granulations containing amoxicillin and the thermally infused granulations containing clavulanate may be separately compressed into bi or tri-layer tablets. Optionally, the thermally infused granulations of amoxicillin or the thermally infused granulations of clavulanate may be blended with amoxicillin or its IR granules and/or clavulanate or its IR granules prior to formulation into controlled release solid dosage forms thereby providing an immediate release portion of these medicaments.

While the above process aspect of the present invention is important it is understood that the present invention also resides in the production of a new type of thermally infused granule with particularly advantageous uses and release characteristics. Therefore, in another aspect of the invention the new products (thermally infused granules and solid dosage forms thereof) constitute a part of the present invention.

Advantageously, certain formulations which may be produced by the above-described process are novel, and comprise further aspects of this invention.

Therefore in a further aspect of the present invention, a controlled release formulation is provided which includes delayed release (DR) granules which comprise a β-lactamase inhibitor and/or a β-lactam antibiotic together with a hydrophobic waxy material.

The β-lactamase inhibitor is suitably clavulanate, the β-lactam antibiotic is suitably amoxicillin, and suitable and preferred waxy materials are as discussed above. The waxy material is suitably included into the granules and as a coating thereupon by the process of thermal infusion of the present invention. The controlled release formulation may suitably also include the various pharmaceutically acceptable excipients etc., as discussed above in addition to the medicaments and the waxy material. The relative ratios of constituents in the controlled release formulation are as discussed above.

The controlled release formulation of this aspect of the invention may suitably comprise TI granules of the antibiotic, e.g. amoxicillin, and/or the inhibitor, e.g. clavulanate, these TI granules being coformulated with IR antibiotic, e.g. amoxicillin, and/or the inhibitor, e.g. clavulanate.

The controlled-release formulation may suitably comprise thermal infusion (TI) granules of the β-lactam antibiotic, e.g. amoxicillin, co-formulated with β-lactam antibiotic in an IR form, e.g. IR granules. Additionally or alternatively the controlled release formulation may suitably comprise TI granules of clavulanate co-formulated with clavulanate in an IR form, e.g. IR granules. Additionally or alternatively the controlled release formulation may comprise TI granules of clavulanate coformulated with TI granules of amoxicillin. Alternatively or additionally the controlled release formulation may comprise TI granules which contain both amoxicillin and clavulanate in the same TI granule, coformulated with IR clavulanate and/or amoxicillin, and optionally with TI granules respectively containing clavulanate and amoxicillin separately.

The controlled release formulation of this aspect of the invention may be provided in a tablet form by compression of the constituents in a tablet press of conventional type. The tablet may be single layered, i.e. containing all of its constituents in one layer, or alternatively it may be multi, e.g. two or three layered. A multi layered tablet may for example contain all of the delayed release medicaments in one layer, and all of the IR medicaments in another, or alternatively may contain all of the antibiotic in one layer and all of the inhibitor in another. Other combinations will be apparent to those skilled in the art.

Glyceryl behenate, as used herein, may be partially or fully substituted by cetyl alcohol, partially hydrogenated vegetable oils (cottonseed, soybean, palm or caster oil) or carnauba wax.

In a further aspect of the invention there is provided a preferred method of transporting quantities, preferably above 50 kg, of potassium clavulanate for manufacturing into controlled release formulations. Clavulanic acid salts are known to undergo a spontaneous exothermic reaction with the release of large quantities of gas and fumes. In addition, ignition of the product may occur. Such decompositions may be initiated by a localized hot spot which may start a train fire reaction throughout the bulk, a "mass effect" (generally observed in quantities above 1 kg) and by a concentrated solution. Currently the following blends which are thermally less sensitive and can be processed using normal pharmaceutical manufacturing equipment including mills are utilized in transporting clavulanic acid.

1. 50% potassium clavulanate+50% amoxycillin trihydrate or sodium amoxicillin
2. 50% potassium clavulanate+50% dried microcrystalline cellulose
3. 50% potassium clavulanate+50% sucrose or 50% fused silica (silicon dioxide)

It has been shown that 80/20 and 50/50 blends of potassium clavulanate and glyceryl behenate do not support train fire when subjected to the 'train fire' test, a test method which indicates whether or not a particular material propagates fire and hence can be transported and/or processed using normal pharmaceutical equipment. Consequently, the preparation of the 70/30 blend was recommended for transportation and processing. This eliminates the need to blend potassium clavulanate with amoxicillin or other excipients which are not required in the formulation, whereas glyceryl behenate can be utilized directly in the formulation. This is particularly advantageous since amoxicillin and potassium clavulanate need to be separately processed in order to achieve desired controlled release profiles. This helps reducing the tablet size as well as the cost of manufacture.

Advantageously, potassium clavulanate is dry granulated with glyceryl behenate in a maximum ratio of potassium clavulanate of 90%, preferably 70%. For manufacturing purposes a ratio of from 80/20 to 50/50 of a clavulanate/glyceryl behenate mixture is preferred.

While the above method aspect of the present invention is important it is understood that the present invention also resides in the production of new, advantageous compositions containing clavulanate and a hydrophobic waxy material. Therefore, in another aspect of the invention the new composition constitutes a part of the present invention.

A further contemplated aspect of the presently invented process and solid dosage forms prepared thereby relates to subsequently coating the prepared solid dosage forms with a controlled release coating.

The following examples describe typical tablet formulations and dissolution profiles of controlled release dosage forms prepared utilizing the present invention, but are not to be interpreted as limiting the scope of the invention in any way.

DISSOLUTION TESTING

The controlled release tablets containing amoxicillin, clavulanic acid or a mixture of amoxicillin and clavulanic acid and prepared by the presently invented process were tested in deionized water following the USP paddle method (Apparatus 2, 100 rpm). The percentage of amoxicillin released is determined by the UV detection and multicomponent analysis while the release profile of clavulanic acid is determined by inductively coupled plasma assay (similar to atomic absorption spectroscopy) for potassium. A minimal degree of degradation of clavulanate was observed when thermal infusion was conducted at the more extreme temperatures, however, the selection of a more appropriate thermal infusion temperature eliminates the degradation of clavulanate.

Clinical Formulations and Experiments

Example I

| Ingredient | Formula A | Formula B |
|---|---|---|
| Amoxicillin trihydrate | 574.0 mg | — |
| Potassium clavulanate | — | 69.3 mg |
| glyceryl behenate | 20.0 mg | 29.7 mg |
| colloidal silicon dixoide | 6.0 mg | 1.0 mg |

The ingredients of Formula A were uniformly blended (batchsize: 20 kgs) using a Hobart blender for 10 minutes. The blend was slugged using a slugging rotary tablet press such as Stokes DD press, and milled using a Fitzmill equipped with a #10 mesh screen. Formula A granules, the sieve fraction passing through #16 mesh screen but collected on the #80 mesh screen, were collected. Similarly, the slugged Formula B granules were obtained. 600.0 mg of Formula A granules was blended with an additional 20.0 mg glyceryl behenate in a Hobart blender (batchsize: 9 kgs) and granulated by the thermal infusion process in a Groen Steam Kettle with modified mixing blades to obtain amoxicillin 'thermal infusion' granules, Formula A1. To prepare the granules of Formula A1 the steam kettle was charged with the blend and the contents were constantly mixed. The kettle was slowly heated to a kettle surface temperature of about 65° C. over a period of about 15 minutes. The contents were granulated over a kettle surface temperature range of 65°–75° C. for about 10 minutes. Then the contents of the kettle were transferred to a wide stainless steel bowl, covered and left to cool to ambient temperature. 620.0 mg of Formula A1 granules was uniformly blended with 120.0 mg of microcrystalline cellulose to obtain amoxicillin compression mix, Formula A2. 90.0 mg of microcrystalline cellulose was uniformly blended with 620.0 mg of Formula A1 granules to obtain amoxicillin compression mix, Formula A3.

214.8 mg of Formula B granules obtained as described above, was uniformly blended with additional 58.0 mg glyceryl behenate (batchsize: 7 kgs) and granulated as described above to obtain Formula B1 granules. In this case the contents of the kettle were granulated over a kettle surface temperature range of 60°–65° C. for about 15 minutes, discharged into a stainless bowl and left to cool to ambient temperature. 267.8 mg of these granules was blended with 20.0 mg of microcrystalline cellulose and 2.2 mg of magnesium stearate to obtain Clavulanate compression mix Formula B3.

148.8 mg of potassium clavulanate was blended with 141.2 mg of glyceryl behenate in a Hobart blender (batchsize: 7 kgs), and the blend thus obtained was granulated as described above, to obtain Clavulanate compression mix Formula B2.

Bilayer Tablets #170 and #180

Bilayer tablets #170 contained 710 mg of Formula A3 granules (equivalent to 500 mg of free amoxicillin) and 290.0 mg of Formula B2 granules (equivalent to 125 mg of free clavulanic acid). The amoxicillin layer of the bilayer tablets #180 contained a blend of 150.0 mg Formula A granules and 555.0 mg of Formula A3 compression mix while the Clavulanate layer contained 290.0 mg of Formula B3 compression mix.

The in-vitro release profiles from these formulations are given in Tables 1 and 2. These formulations were orally administered to six healthy volunteers in a preliminary crossover clinical study. The mean plasma concentrations observed in these healthy volunteers are given in Tables 1 and 2. The clinical data suggests that the controlled release of both amoxicillin and potassium clavulanate were achieved.

TABLE 1

Dissolution Data for #170 Tablets

| Time, hour | Amoxicillin In-vitro, mg | Amoxicillin Plasma Conc., ug/ml | Clavulanic Acid In-vitro, mg | Clavulanic Acid Plasma Conc., ug/ml |
|---|---|---|---|---|
| 0.5 | 15 | 0.08 | 27.5 | 0.0902 |
| 1 | 35 | 0.828 | 50 | 0.2898 |
| 1.5 | | 3.279 | | 0.3752 |
| 2 | | 3.691 | | 0.407 |
| 3 | 110 | 5.351 | 95 | 0.3928 |
| 4 | | 4.546 | | 0.2998 |
| 5 | | 3.261 | | 0.2212 |
| 6 | 180 | 2.131 | 101.2 | 0.1188 |
| 7 | | 1.071 | | 0.0317 |
| 8 | | 0.4772 | | 0 |
| 10 | | 0.1808 | | 0 |
| 12 | | | | |

TABLE 2

Dissolution Data for #180 Tablets

| Time, hour | Amoxicillin In-vitro, mg | Amoxicillin Plasma Conc., ug/ml | Clavulanic Acid In-vitro, mg | Clavulanic Acid Plasma Conc., ug/ml |
|---|---|---|---|---|
| 0.5 | 255 | 1.169 | 87.5 | 0.4272 |
| 1 | 295 | 4.62 | 110 | 1.116 |
| 1.5 | | 7.08 | | 1.328 |
| 2 | | 6.585 | | 1.485 |
| 3 | 370 | 4.517 | 128.7 | 0.8177 |
| 4 | | 3.163 | | 0.3785 |
| 5 | | 1.969 | | 0.1775 |
| 6 | 420 | 0.901 | 126.2 | 0.0633 |
| 7 | | 0.492 | | 0.009 |
| 8 | | 0.262 | | 0 |
| 10 | | 0.151 | | 0 |
| 12 | | 0.0868 | | 0 |

Examples 2 through 5 were performed on batch sizes of 20–50 g. Granulation at the stated temperature was maintained for about 10 minutes.

Example 2

TABLE 3

| Ingredient | Formula #1 | Formula #2 | Formula #3 | Formula #4 |
|---|---|---|---|---|
| Amoxicillin trihydrate | 286.9 | 286.9 | — | — |
| K. Clavulanate | — | — | 74.4 | 74.4 |
| glyceryl behenate | 63.1 | 63.1 | 74.4 | 74.4 |
| microcrystalline cellulose | — | — | 21.2 | — |
| microcrystalline cellulose | — | 90.0 | — | — |
| | 350.00 | 440.0 | 170.0 | 148.8 |

Formulas #1 & 2 were thermally infused at 80°–85° C. while Formulas #3 & 4 were thermally infused at 65°–70° C. to minimize possible degradation of potassium clavulanate. These formulations provide prolonged release or the active components (Table 4).

TABLE 4

Dissolution Data for Formulas #1 to 4
% Release

| Time (hr) | Formula #1 amoxicillin | Formula #2 amoxicillin | Formula #3 clavulanate | Formula #4 clavulanate |
|---|---|---|---|---|
| 0.5 | 0.5 | 13.0 | 37.0 | 29.0 |
| 1.0 | 7.0 | 20.5 | 49.0 | 40.0 |
| 3.0 | 13.0 | 40.5 | 79.0 | 63.0 |
| 6.0 | 19.0 | 64.5 | 93.0 | 76.0 |

Example 3

The need for thermal infusion instead of dry blending is demonstrated by preparing two direct compression formulations of amoxicillin and clavulanic acid and testing for dissolution profiles.

TABLE 5

Formulations Details

| Ingredient | Formula #5 | Formula #6 |
|---|---|---|
| Amoxicillin trihydrate | 286.9 | — |
| K. Clavulanate | — | 74.4 |
| glyceryl behenate (Compritol) | 143.5 | 74.4 |
| microcrystalline cellulose (avicel) | 16.6 | 21.2 |
| Colloidal silicon dioxide | 3.0 | — |
| | 450.0 | 170.0 |

The ingredients of Formulas #5 and #6 were separately dry blended using a suitable mixer for 5–10 minutes and compressed into tablets using appropriate dies and punches. The tablets thus obtained were subjected to dissolution testing. Both formulations have been found to release nearly 100% of the active in less than 3 hours (Table 6), and thus would not provide a sufficient control release profile for pharmaceutical utilization.

TABLE 6

Dissolution Data for Formulas #5 and #6
% Release

| Time (hrs) | Formula #5 amoxicillin | Formula #6 clavulanate |
|---|---|---|
| 0.5 | 90.0 | 55.0 |
| 1.0 | 95.0 | 82.0 |
| 3.0 | 97.0 | 98.0 |

Example 4

TABLE 7

Formulation Details

| Ingredient | Formula #7 | Formula #8 | Formula #9 |
|---|---|---|---|
| Amoxicillin trihydrate | 286.9 | 258.2 | — |
| K. Clavulanate | — | 29.8 | 148.8 |
| glyceryl behenate (Compritol) | 50.5 | 62.0 | 148.8 |
| Cetyl alcohol | 12.6 | — | — |
| microcrystalline cellulose (Avicel) | — | — | 22.4 |
| | 350.00 | 350.00 | 320.0 |

The thermal infusion temperatures for Formulas #7 to 9 were, respectively; 70°–75° C., 65°–70° C., and 55°–60° C. The in-vitro release profile data represented in Table 8 suggest that any of these formulations can provide long lasting delivery of the active component(s) in the body of the patient on oral administration.

TABLE 8

Dissolution Data for Formulas #7 to 9
% Release

| Time (hrs) | amoxicillin Formula #7 | amoxicillin and clavulanate Formula #8 | clavulanate Formula #9 |
|---|---|---|---|
| 0.5 | 3.0 | 4.0:36.0 | 29.0 |
| 1.0 | 5.0 | 7.0:50.0 | 40.0 |
| 3.0 | 8.0 | 13.0:79.0 | 65.0 |
| 6.0 | 11.0 | 19.0:90.0 | 81.0 |

Example 5

TABLE 9

Formulation Details

| Ingredient | Formula #10 | Formula #11 |
|---|---|---|
| Amoxicillin trihydrate | — | — |
| K. Clavulanate | 150.0 | 150.0 |
| microcrystalline cellulose (Avicel) | 150.0 | 150.0 |
| glyceryl behenate (Compritol) | 150.0 | 120.0 |
| Cetyl alcohol | — | 30.0 |
| | 450.0 | 450.0 |

Ingredients of Formulas #10 and 11 were blended using a suitable mixer and thermally infused at a thermal infusion temperature of 65°–70° C. and 55°–60° C. respectively for 10 minutes.

The dissolution data presented in Table 10 suggests that prolonged release of clavulanic acid can be obtained by using the process of this invention.

TABLE 10

Dissolution Data for Formulas #10 to 11
% Release

| Time (hrs) | Formula # 10 clavulanate | Formula # 11 clavulanate |
|---|---|---|
| 0.5 | 29.0 | 30.0 |
| 1.0 | 40.0 | 44.0 |
| 3.0 | 65.0 | 81.0 |
| 6.0 | 81.0 | 91.0 |

Example 6

TABLE 11

Cimetidine Formulation Details

| Ingredient | mg/tablet Formula# 12 | mg/tablet Formula# 13 |
|---|---|---|
| Cimetidine | 200.0 | 200.00 |
| glyceryl behenate (Compritol) | 104.3 | 42.85 |
| microcrystalline cellulose (Avicel) | 43.5 | 42.85 |
| Total | 347.8 | 285.7 |

The above ingredients of cimetidine formulations were blended using a Hobart blender (batchsize 7–8 kgs). The blends were roller compacted using a roller compactor such as Fitzpatrick Model L83 Roller Compactor. The sieve setup was equipped with #20 and #60 mesh screens. The granules passing through the #20 screen and residing on the #60 mesh screen were subjected to thermal infusion in a fluid bed granulator such as UniGlatt (batchsize: 500 gms). The UniGlatt was charged with the granules and fluidized. The product temperature was raised from ambient (18° C.) to about 50° C. over a period of about 10 minutes. The granules were held at that temperature for about 25 minutes and cooled to ambient temperature over a period of about 15 minutes. The cooled granules were compressed into tablets. As suggested from the release profile data presented in Table 12, controlled release of the medicament was achieved.

TABLE 12

Release Profiles of Cimetidine

| Time (hour) | % Cimetidine Released Formula# 12 | % Cimetidine Released Formula# 13 |
|---|---|---|
| 1.0 | 8.5 | 11.8 |
| 3.0 | 14.9 | 25.0 |
| 6.0 | 22.0 | 36.0 |
| 9.0 | 27.0 | 45.0 |
| 12.0 | 32.0 | 51.0 |

The above Examples demonstrate the unprecedented diversity of utility of the present invention in that large quantities of controlled release solid dosage forms of highly water soluble, heat labile-moisture sensitive compounds (clavulanate); compounds which are only slightly soluble in water (amoxicillin), compounds which are moderately soluble in water (Cimetidine) and co-formulations thereof (Amoxicillin/Clavulanate) were all successfully prepared thereby.

While the preferred embodiments of the invention are illustrated by the above, it is to be understood that the invention is not limited to the precise instructions herein disclosed and that the right to all modifications coming within the scope of the following claims is reserved.

What is claimed is:

1. A process for preparing controlled release solid dosage forms of pharmaceutically active materials which comprises:

(a) blending a pharmaceutically active material, a hydrophobic waxy material and optional additives;

(b) compacting, milling and screening said blend; and (c) thermally infusing the screened blend in a granulator at a thermal infusion temperature to yield thermal infusion granules.

2. The process of claim 1 which further comprises formulating the prepared thermal infusion granules into solid dosage forms.

3. The process of claim 2 which comprises:

(a) blending a pharmaceutically active material and a hydrophobic waxy material;

(b) compacting, milling and screening said blend;

(c) thermally infusing the screened blend in a granulator at a temperature of from about 5° C. to about 25° C. below the extrapolated onset temperature of the hydrophobic waxy material;

(d) formulating the prepared thermal infusion granules into solid dosage forms.

4. The process of claim 3 wherein the thermal infusion takes place at a temperature of from about 5° C. to about 15° C. below the extrapolated onset temperature of the hydrophobic waxy material.

5. The process of claim 3 wherein the pharmaceutically active material is moisture sensitive, heat labile or moisture sensitive and heat labile.

6. The process of claim 3 wherein the pharmaceutically active material is an antibacterial agent.

7. The process of claim 3 wherein the pharmaceutically active material is clavulanate.

8. The process of claim 7 wherein clavulanate is co-formulated with amoxicillin trihydrate.

9. The process of claim 6 wherein the antibacterial agent is amoxicillin trihydrate and the hydrophobic waxy material is glyceryl behenate.

10. The process of claim 3 wherein a pharmaceutically acceptable excipient is added to step a.

11. The process of claim 9 wherein a pharmaceutically acceptable excipient is added to step d.

12. The process of claim 3 wherein the pharmaceutically active material is clavulanate and the hydrophobic waxy material is glyceryl behenate.

13. The process of claim 1 which comprises:

(a) blending clavulanate and glyceryl behenate in a range of from about 20% to 80% by weight of clavulanate;

(b) compacting, milling and screening said blend;

(c) thermally infusing the screened blend in a fluid bed granulator by raising the temperature of the fluidized granules from ambient (about 18° C.) to about 50° C. over a period of about 10 minutes, maintaining the temperature at about 50° C. for about 25 minutes and cooling to ambient temperature over a period of about 15 minutes.

14. The process of claim 13 in which the percentage of clavulanate used in step (a) is about 55%.

15. The process of claim 1 which comprises:

(a) blending amoxicillin trihydrate and glyceryl behenate in a range of from about 50% to 98% by weight of amoxicillin trihydrate;

(b) compacting, milling and screening said blend;

(c) thermally infusing the screened blend in a fluid bed granulator by raising the temperature of the fluidized granules from ambient (about 18° C.) to about 50° C. over a period of about 10 minutes, maintaining the temperature at about 50° C. for about 25 minutes and cooling to ambient temperatures over a period of about 15 minutes;

(d) blending the prepared cooled granules with microcrystalline cellulose in a range of from about 5% to 50% by weight of microcrystalline cellulose.

16. The process of claim 15 in which the percentage of amoxicillin trihydrate used in step (a) is about 90% and the percentage of microcrystalline cellulose used in step d is about 15%.

17. The process of claim 13 which further comprises uniformly blending the prepared thermally infused granules with IR granules of clavulanate and glyceryl behenate wherein the IR granules have a range of from about 20% to 80% by weight of clavulanate.

18. The process of claim 17 in which the percentage of clavulanate used in the IR granules is about 70%.

19. The process of claim 15 which further comprises blending the prepared thermally infused granules with IR granules of amoxicillin trihydrate and glyceryl behenate wherein the IR granules have a range from about 75% to 98% by weight of amoxicillin trihydrate.

20. The process of claim 19 in which the percentage of amoxicillin trihydrate used in the IR granules is about 90%.

21. The process of preparing solid dosage forms of amoxicillin trihydrate and clavulanate which comprises co-formulation of granules prepared in claim 18 and granules prepared in claim 20.

22. The process of preparing a controlled release solid dosage form containing amoxicillin trihydrate and clavulanate which comprises compressing granules prepared as in claim 18 and granules prepared as in claim 20 into a bilayer tablet.

23. The process of claim 2 wherein the pharmaceutically active material is cimetidine.

24. The process of claim 2 wherein the pharmaceutically active material is lithium carbonate.

25. The process of claim 1 which comprises:

(a) blending the pharmaceutically active material and the hydrophobic waxy material;

(b) thermally infusing said blend;

(c) milling and screening the thermally infused blend.

26. The process of claim 3 in which the pharmaceutically active material is compacted prior to step a.

27. The process of claim 1 which comprises:

(a) blending amoxicillin trihydrate and glyceryl behenate in a range of from about 81% to 98% by weight of amoxicillin trihydrate;

(b) compacting, milling and screening said blend;

(c) thermally infusing the screened blend in a fluid bed granulator at a temperature above the extrapolated onset temperature of glyceryl behenate;

(d) blending the prepared cooled granules with microcrystalline cellulose in a range of from about 5% to 50% by weight of microcrystalline cellulose.

28. The process claim 27 in which the percentage of amoxicillin trihydrate used in step (a) is about 90% and the percentage of microcrystalline cellulose in step (d) is about 15%.

29. The process of claim 27 which further comprises blending the prepared thermally infused granules with IR granules of amoxicillin trihydrate and glyceryl behenate wherein the IR granules have a range of from about 75% to 98% by weight of amoxicillin trihydrate.

30. The process of preparing a controlled release solid dosage form containing amoxicillin trihydrate and clavulanate which comprises compressing granules prepared as in claim 17 and granules prepared as in claim 29 into a bilayer tablet.

31. The process of claim 23 which further comprises blending the prepared thermally infused granules with IR granules of cimetidine and glyceryl behenate.

32. The process of claim 1 which comprises:

(a) blending a pharmaceutically active material and a hydrophobic waxy material;

(b) compacting, milling and screening said blend;

(c) thermally infusing the screened blend in a granulator at a temperature of from about 5° C. to about 25° C. below the extrapolated onset temperature of the hydrophobic waxy material.

33. The process of claim 25 which further comprises formulating the prepared thermal infusion granules into solid dosage forms.

34. The process of claim 1 which comprises:

(a) blending the pharmaceutically active material and the hydrophobic waxy material in a range of from about 81% to 98% by weight of the pharmaceutically active material;

(b) compacting, milling and screening said blend;

(c) thermally infusing the screened blend in a fluid bed granulator at a temperature above the extrapolated onset temperature of the hydrophobic waxy material.

* * * * *